United States Patent [19]
Young et al.

[11] Patent Number: 5,597,731
[45] Date of Patent: Jan. 28, 1997

[54] PLANT PROPAGATION SYSTEM

[75] Inventors: Roy E. Young, Six Mile; Jeffrey W. Adelberg, Clemson, both of S.C.

[73] Assignee: Clemson University, Clemson, S.C.

[21] Appl. No.: 458,988

[22] Filed: Jun. 2, 1995

Related U.S. Application Data

[62] Division of Ser. No. 189,499, Jan. 31, 1994, Pat. No. 5,525,505.

[51] Int. Cl.$^6$ ............................. C12M 3/00; A01G 31/02
[52] U.S. Cl. .................................. 435/284.1; 435/286.5; 435/289.1; 435/292.1; 435/294.1; 435/297.1; 435/305.1; 435/809; 435/297.2; 435/297.5; 435/303.1; 435/286.6; 47/59; 47/60; 47/61; 47/62; 47/66
[58] Field of Search .......................... 435/240.1, 240.4, 435/240.45, 284, 300, 301, 800, 809, 286.5, 284.1, 289.1, 292.1, 294.1, 297.1, 297.2, 305.1, 305.4, 297.5, 286.6, 303.1; 47/59, 60, 61, 62, 66, 81, 101

[56] References Cited

U.S. PATENT DOCUMENTS

| | | |
|---|---|---|
| 3,578,431 | 5/1971 | Ingestad et al. |
| 3,610,740 | 10/1971 | Aparicio ................................. 350/312 |
| 4,043,903 | 8/1977 | Dor . |
| 4,320,594 | 3/1982 | Raymond . |
| 4,382,348 | 5/1983 | Kitsu et al. |
| 4,531,324 | 7/1985 | Yang et al. |
| 4,626,071 | 12/1986 | Wada et al. ............................ 350/311 |
| 4,669,217 | 6/1987 | Fraze . |
| 4,754,877 | 7/1988 | Johansson et al. |
| 4,887,386 | 12/1989 | Minshull ................................ 47/48.5 |
| 4,908,315 | 3/1990 | Kertz . |
| 4,934,096 | 6/1990 | Bentvelsen . |
| 4,975,377 | 12/1990 | Key . |
| 5,001,859 | 3/1991 | Sprung . |
| 5,022,181 | 6/1991 | Longstaff ................................ 47/31 |
| 5,049,505 | 9/1991 | Sei . |
| 5,054,234 | 10/1991 | Cassells . |
| 5,088,231 | 2/1992 | Kertz . |

(List continued on next page.)

OTHER PUBLICATIONS

Hale et al., Plastic Films as Plant Tissue Culture Vessels (ASAE meeting presentation booklet, Dec. 1990 International Wnter Meeting, Chicago, Illinois).

Phytasource, Sigma Chemical Company, Spring 1990 vol. 1, No. 1).

Hale et al., Plant Micropropagation Bioreactor Development (ASAE meeting presentation Dec. 17–20, 1991 Chicago, Illinois).

Hale et al., Bioreactor Development for Continual–Flow, Liquid Plant Tissue Culture, Acta Horticulturae, 319, 1992 (pp. 107–112).

*Primary Examiner*—Esther Kepplinger
*Assistant Examiner*—Milton I. Cano
*Attorney, Agent, or Firm*—Dority & Manning, P.A.

[57] ABSTRACT

A plant propagation system and method are provided for promoting the growth of plant tissue into small plantlets. The plant propagation system includes sealed, semipermeable membrane vessels for completely enclosing plant material therein. The sealed vessels generally are translucent and permeable to gases and liquids while remaining impermeable to biological contaminates. Plant tissue originally extracted from a parent plant can be placed within the sealed vessels and grown heterotrophically. Once the plant material has developed the capability to photosynthesize, the sealed vessels can be transferred to a greenhouse environment for photoautotrophic growth. Once in a greenhouse environment, the sealed vessels are supported in trays and exposed to light, gases, water and a liquid nutrient solution for optimizing growth. A central controller can be included in order to automate the system for controlling the flow of fluids in and out of the vessel support trays while also monitoring system conditions. A disinfectant can also be circulated within the system for destroying biological contaminants in the tray and outside the sealed vessels for maintaining an aseptic environment.

30 Claims, 4 Drawing Sheets

U.S. PATENT DOCUMENTS

| | | |
|---|---|---|
| 5,104,527 | 4/1992 | Clinkenbeard . |
| 5,119,588 | 6/1992 | Timmis . |
| 5,139,956 | 8/1992 | Schick et al. . |
| 5,171,683 | 12/1992 | Kertz . |
| 5,184,420 | 2/1993 | Papadopoulos et al. . |
| 5,186,895 | 2/1993 | Onofuse et al. . |
| 5,212,906 | 5/1993 | Okuno et al. . |
| 5,225,342 | 7/1993 | Farell . |
| 5,324,657 | 6/1994 | Tanny . |

PLANT PROPAGATION SYSTEM

This is a division of application Ser. No. 08/189,499, filed Jan. 31, 1994, now U.S. Pat. No. 5,525,505.

BACKGROUND OF THE INVENTION

The present invention relates generally to a plant propagation system, and more particularly to an aseptic propagation system and process for promoting the growth of plant tissue into transplants.

Micropropagation, sometimes referred to as tissue culture propagation, is the process of growing new plants from a piece of plant tissue that has been extracted from a parent plant with desired characteristics. Micropropagation has recently grown in popularity as a preferred plant propagation technique for a wide range of horticultural crops because of high production efficiency and greater uniformity of the resulting plants. The process results in the mass reproduction of plants having certain desirable characteristics since substantially all of the plants produced are genetically identical to and have all of the desirable traits of the parent. Micropropagation is an especially useful process for genetically engineered plants, high-value transplants, seedless fruits and vegetables, certified disease free plant material and all other plants that cannot be produced from seed economically or uniformly.

In general terms, micropropagation typically includes first selecting a parent plant. The parent plant should be healthy and should have the desired traits that are needed in the next generation plants. A tissue sample is then extracted from the parent. The sample is typically meristematic tissue which is undifferentiated tissue capable of dividing and giving rise to other meristemic tissue as well as specialized tissue types. Meristematic tissue is found in growth areas such as at the tips of stems or at lateral buds. The tissue sample (explant) is disinfested and then placed in a controlled environment and supplied essential nutrients for promoting growth.

Growth of the plant tissue sample into a small plant occurs in four commonly referred to stages. First, growth of the explant is established in a sterile environment. Second, high prolifferation of explant is promoted by repeated selection of small pieces of tissue containing vegetative buds, or other specialized propagative structures (e.g. bulbets, protocorm-like bodies (PLB), microtubers, somatic embryos). The third stage involves forming a shoot from the vegetative bud. The fourth stage involves forming a root on the shoot, thereby completing the development of a whole plant from the plant tissue.

During the first and second stage of growth, the plant tissue is made up of small rapidly dividing cells with high metabolic requirements for energy. The tissue is incapable of carrying out adequate photosynthesis to meet this high demand.

Consequently, initial growth of the tissue is done heterotrophically. Heterotrophic growth is where the organism obtains nourishment and energy from the ingestion and breakdown of organic matter. During this phase, the plant tissue is typically not exposed to light and is fed a growth medium containing organic carbon. The organic carbon is usually obtained from sugars such as sucrose.

In the third stage of growth, leaves and shoots expand and the plant tissue becomes more capable of photosynthesizing. The plant tissue, when exposed to light, gases, water and essential nutrients, derives energy photoautotrophically through the process of photosynthesis. Photoautotrophic growth is where an organism synthesizes organic nutrients by deriving energy from light. In other words, during autotrophic growth, the plant tissue is capable of making its own food which it cannot do adequately during the other stages.

Traditionally, tissue culture propagation has been done on agar or semisolid mediums for providing nutrients and organic carbon to the plant material. The nutrient mediums have been contained in small glass or plastic containers open to the atmosphere for allowing needed gas exchange. However, many problems have been encountered using these techniques. For instance, the largest of these problems has been contamination. Microorganisms such as bacteria, fungus, viruses, molds, yeast or other small plants, which thrive on the organic compounds in the mediums, can attack and kill or inhibit the growth of vulnerable plant tissue samples. In order to prevent contamination, the tissue samples have to be placed in a sterile and controlled environment. As such, all work has typically been confined to the laboratory.

Another disadvantage to using agar or semisolid mediums is the expense or production costs involved in growing the plants. First, high costs are involved in maintaining stringent aseptic environments as described above. The facilities and equipment needed are also expensive necessities. Further, using agar or semisolid liquid mediums requires large amounts of manual labor. For instance, the growing plantlets must be frequently transferred to new vessels with fresh media. This work is very labor intensive because the fragile plants are typically embedded in the spent media and need to be carefully removed. These multiple transfers also limit the ability to automate the system.

Recently, many attempts have been made to develop a plant tissue propagation system that does not require growing plants on agar or semisolid mediums. Instead, the plants are fed a liquid nutrient solution. For instance, U.S. Pat. No. 5,225,342 to Farrell discloses an artificial replacement for the vascular and support functions normally provided by the root system of a plant. The apparatus includes placing a totipotent plant cell on an artificial xylem surface. Xylem is the principal water and mineral conducting tissue in vascular plants. Nutrient solutions are applied in a manner which encourages the growth of the cell to form aerial portions of the plant and which essentially prohibits the growth of plant roots.

In one embodiment, a growth chamber for a vascular plant having xylem and phloem tissue is provided. The chamber is constructed from a high impact polystyrene or polycarbonate material and has three trays for holding various liquids. Inside the chamber, a plurality of totipotent plant cells or explant tissue is inserted through incisions in a sponge which is placed on an artificial xylem surface. A nutrient solution, circulated through the lower tray, is fed to the plant tissue through the artificial xylem. The artificial xylem is preferably constructed of small tubules made from polypropylene. A rinse solution is introduced into the upper tray where it falls onto the sponge where the plant tissue has been inserted. The rinse solution then flows through the sponge to the middle tray where it exits the chamber. Preferably, the rinse media is a sterile, deionized aqueous solution adjusted to the physiological pH of the plant, but any solution which is isotonic and capable of removing endotoxins or waste material exuded by the plant tissue into the sponge is acceptable. Further, the chamber includes a top cover which has a carbon dioxide inlet and a microbial shield-water vapor diffusion membrane. The membrane, preferably made from polyethylene, permits gas transfer without the introduction of microbial contamination into the chamber.

U.S. Pat. Nos. 5,171,683 and 4,908,315, both to Kertz, disclose an integument and method for microbe propagation and tissue culturing. Here, a sealed integument is made of a semipermeable and translucent membrane which allows light transmission and gas exchange but seals out biological contaminants. A plant, seeds, or plant tissue is placed inside the sealed integument along with a growth medium such as soil or a liquid media. The integument is liquid impermeable so that a liquid or semisolid growth medium cannot escape and dry out the plant. The integument is made from a polyethylene material.

A method and apparatus for culturing autotrophic plants from heterotrophic plant material is disclosed in Timmis et al., U.S. Pat. No. 5,119,588. In this patent, plant material is embedded in a plug of particulate medium having soil-like properties. The plug should be sterile and may contain water, mineral nutrients or plant hormones. The plug and plant material are then placed in a bag which is preferably made of a material which allows the passage of light and gases necessary for plant growth and development from the ambient environment to the interior of the bag. The bag preferably also passes water vapor at a slow rate from the interior of the bag to the ambient environment for humidity control inside the bag. Candidate bag materials include high density polyethylene, polypropylene, and fluorinated ethylenepropylene.

Other plant growing systems are discussed and disclosed in U.S. Pat. No. 5,212,906 to Okuno et al., U.S. Pat. No. 5,184,420 to Papadopoulis et al., U.S. Pat. No. 5,088,231 to Kertz, and U.S. Pat. No. 5,049,505 to Sei.

Although disclosing an assortment of plant propagation and growing systems, the prior art still has its drawbacks and deficiencies. For instance, some of the prior art fails to provide a method or apparatus that is truly effective at preventing contamination of the growing plant material. For instance, in many prior art devices the plant material is vulnerable to attack once the growth medium becomes infected with harmful microorganisms. Also, many of the prior art methods fail to provide an efficient way to replace or replenish the plant growth medium once it becomes spent. Further, once sealed in a container, problems have been encountered in the past in getting the small plantlets to photosynthesize.

SUMMARY OF THE INVENTION

The present invention recognizes and addresses the foregoing disadvantages, and others of prior art constructions, and methods.

Accordingly, it is an object of the present invention to provide a plant propagation system.

It is another object of the present invention to provide a new method for propagating plant material.

It is a further object of the present invention to provide a plant propagation system and method that does not rely on agar or semisolid growing mediums.

It is another object of the present invention to provide a plant propagation system and method that prevents contamination of the growing plant material.

It is still another object of the present invention to provide a plant propagation system and method that is automated for mass production of plants.

It is another object of the present invention to provide a plant propagation system and method that continually replenishes the nutrients and gasses necessary for plant growth.

It is a further object of the present invention to provide a plant propagation system and method that facilitates the transportation of plant material.

These and other objects are achieved by providing a plant propagation system for producing small, uniform plants with desired traits by growing and developing plant tissue under aseptic conditions. The plant propagation system includes a vessel support tray for receiving a plurality of sealed semipermeable membrane vessels containing plant material therein. The vessel support tray further includes a fluid retaining chamber adapted to contain and circulate various fluids for contact with the vessels. A growth media reservoir means supplies a growth media to the fluid retaining chamber of the vessel support tray for absorption by the plant material. Valved conduit means connects the vessel support tray with the growth media reservoir and is further used for regulating the flow of the growth media therebetween. The propagation system further includes a central control means in communication with at least certain elements of the system for automatic control thereof.

Optionally, the plant propagation system can include a disinfectant reservoir means for periodically supplying a disinfectant to the vessel support tray for destroying microorganisms within the tray and on the outside of the sealed vessels. Further, a water source can be connected to the system for supplying water for rinsing the vessel support tray and the vessels after circulating the disinfectant. The water can also be used for absorption by the plant tissue during photosynthesis. The system can also include a carbon dioxide source for supplying carbon dioxide to the vessel support tray for diffusion into the sealed vessels. Further, a spectral filter means can be added for filtering light such that light rays at a desired intensity and wavelength reach the plant tissue. The spectral filter means can include a colored piece of material or translucent channelized glazing filled with a light filtering liquid.

The central control means included within the propagation system can include a programmable electronic device such as a microprocessor. The central control means can control the flow and level of liquids and can be connected to various monitoring devices for monitoring other system conditions. For instance, the system can include a pH meter, a conductivity meter, and/or a thermocouple, etc., each capable of transmitting signals to the central control means.

Another present exemplary embodiment of the present invention concerns a plant propagation system for growing plant tissue and producing small plants capable of being transplanted into soil. The system includes a plurality of sealed, semipermeable membrane vessels for containing growing plant material therein. Each of the vessels has a top membrane portion and a bottom membrane portion. The top membrane portion is translucent and gas permeable but is impermeable to microorganisms. The bottom membrane portion is liquid permeable and also impermeable to microorganisms. The vessels allow necessary nutrients and gases to diffuse therein for promoting the development of the plant material while preventing the influx of biological contaminants. As such, the present invention is also directed to a novel container for enclosing plant material.

A vessel support tray having a top plate defines a plurality of openings for receiving the semipermeable vessels. The tray includes a fluid retaining chamber adapted to contain and circulate various fluids for contact with the vessels. A growth media reservoir means and a disinfectant reservoir means supply growth media and disinfectant respectively to the vessel support tray. A water source is also connected to the system for rinsing the tray and for providing water to the plant material. Valved conduit means interconnects the growth media reservoir, the disinfectant reservoir, and the water source to the vessel support tray and provides a means for regulating the flow of the various fluids. The fluids are fed to the tray in a preselected pattern at predetermined times for optimally growing the plant material.

The plant propagation system can further include a central control means such as a programmable electronic device for automatically controlling the valved conduit means and automating the system. Again, other monitoring instruments and probes can be connected to the central control means for monitoring and correcting other system conditions.

The plant propagation system can also include a cooling and heating means for maintaining optimal temperatures within the sealed vessels. The sealed vessels can contain porous materials such as cellulose plugs for supporting any root structure growing from the plant material.

The growth media used can include a hydroponic solution containing necessary plant nutrients while the disinfectant can include a sodium hypochlorite solution at a concentration at about 0.1% to about 10% by volume. A carbon dioxide source can also be added to the system for feeding carbon dioxide to the vessel support tray.

As described above, the sealed vessels have a top membrane portion and a bottom membrane portion. The top membrane portion can be made from a translucent polypropylene film while the bottom membrane portion can be made from a stretched microporous polypropylene film. Regardless, the top and bottom membranes should have a pore size no larger than about 0.2 microns for preventing the passage of microorganisms. To be gas permeable, the membranes should have a pore size of about 0.01 microns while a liquid and gas permeable membrane should have a pore size of from about 0.01 microns to about 0.2 microns. In one embodiment, the top membrane portion can include two sections where one section is gas permeable only while the other section is gas and liquid permeable.

The present invention further includes a method of propagating plant material. The method involves the steps of placing living plant material into a sealed semipermeable membrane vessel where the vessel is gas and liquid permeable while remaining impermeable to microorganisms. The vessel is then subjected to a lighted atmosphere containing oxygen and carbon dioxide for diffusion therein for use by the plant material. The vessel is also contacted with a growth media wherein necessary nutrients, liquids, gases and light diffuse into the vessel for promoting the development and growth of the plant material while preventing the influx of biological contaminants.

The method of propagating plant material can also include the step of periodically contacting the vessel with a disinfectant such as a sodium hypochlorite solution. The disinfectant is for destroying any microorganisms on the outside of the vessel. Preferably, the vessel is then rinsed with water after the disinfectant is used.

In a similar method for propagating plant tissue, the plant tissue is completely enclosed into a sealed semipermeable membrane vessel. The method involves diffusing gases into the vessel, transmitting light into the vessel, and contacting the vessel with a plant growth media. The plant tissue can then absorb the gases, light and plant growth media for proper growth and development.

As before, the vessel can also be periodically subjected to a disinfectant for a period of time sufficient to destroy any biological contaminants on the outside of the vessel without permitting the diffusion of the disinfectant therein. After using the disinfectant, the vessel should be rinsed with water.

In one particular arrangement, the sealed vessel is contacted with water during daylight hours while during the night, the vessel is contacted with a plant growth media. Such an arrangement limits the growth of algae or other small plants within the system.

Further, the present invention also includes a method of developing undifferentiated plant tissue into plants capable of being transplanted into soil by first placing a piece of viable and poorly differentiated plant tissue into the sealed, semipermeable membrane vessels described above. Again, the vessels are permeable to gases and liquids while remaining impermeable to microorganisms. The sealed vessel containing the poorly differentiated plant tissue is contacted with a solution containing organic carbon for absorption by the plant tissue for promoting heterotrophic growth. Once the plant tissue is capable of photosynthesizing, the vessel is then exposed to light, oxygen, carbon dioxide and a hyproponic solution for promoting photoautotrophic growth. As such, the plant tissue develops into a small plant without ever being removed from the sealed vessel and without being exposed to pathogenic microorganisms.

Other objects, features and aspects of the present invention are discussed in greater detail below.

BRIEF DESCRIPTION OF THE DRAWINGS

A full and enabling disclosure of the present invention, including the best mode thereof, to one of ordinary skill in the art is set forth more particularly in the remainder of the specification, including reference to the accompanying figures, in which.

Figure 1:
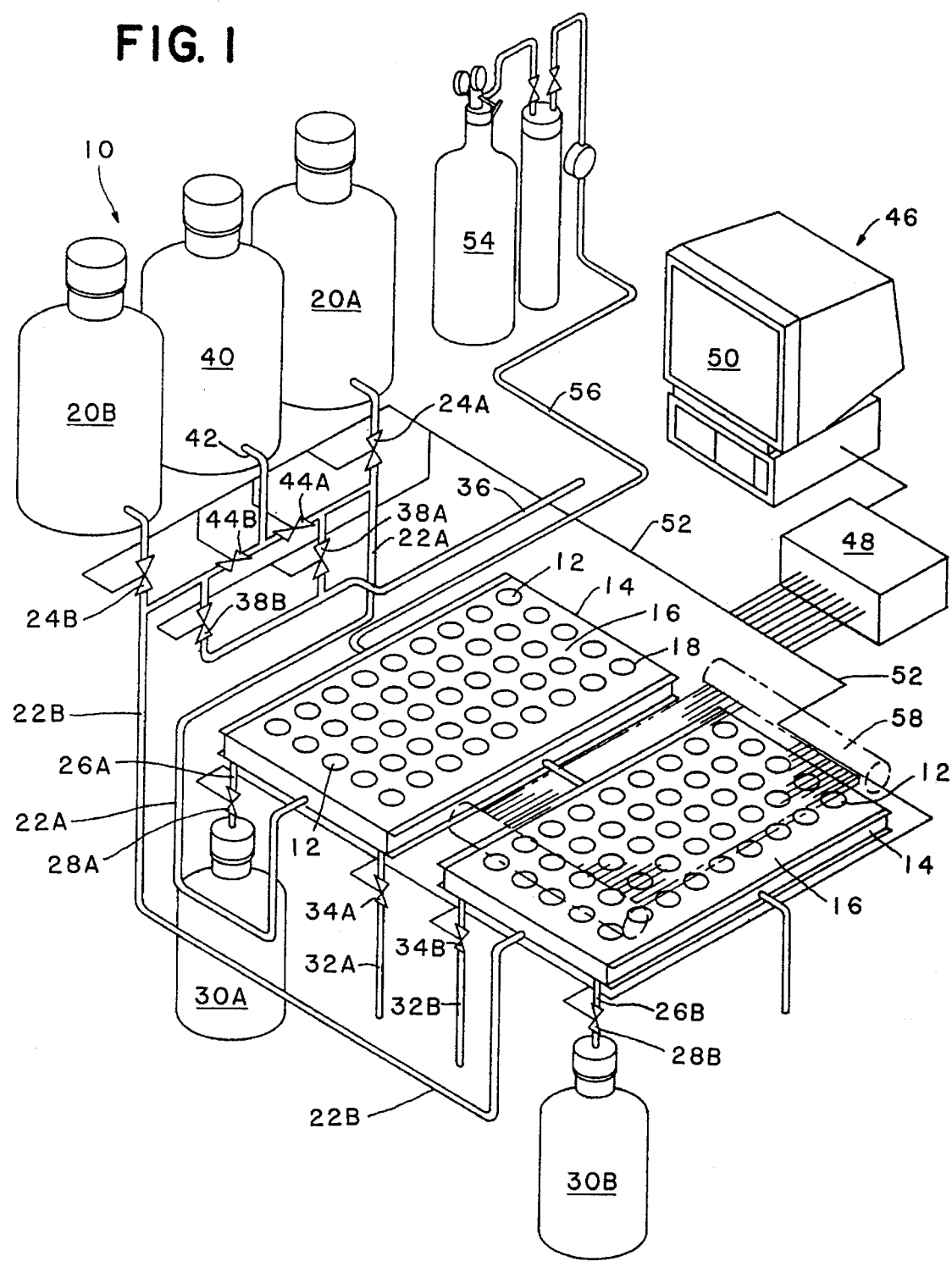
FIG. 1 is a perspective view of an embodiment of a plant propagation system in accordance with the present invention.

Repeat use of reference characters in the present specification and drawings is intended to represent same or analogous features or elements of the invention.

DETAILED DESCRIPTION OF PREFERRED EMBODIMENTS

It is to be understood by those of ordinary skill in the art that the present discussion is a description of exemplary embodiments only, and is not intended as limiting the broader aspects of the present invention, which broader aspects are embodied in the exemplary constructions.

The present invention is generally directed to a plant propagation system and method. More specifically, the system is designed for growing plant tissue that has developed the ability to carry out photosynthesis or is designed to create an environment for promoting photoautotrophic growth, prior to removing plant tissue from an organic media. Growth of the plant material continues in the system until the plants are ready to be transplanted in soil or need to be transported to a different location.

Referring to FIG. 1, a plant propagation system generally 10 is shown. Plant propagation system 10 includes a plurality of sealed, semipermeable membrane vessels 12 for containing and completely enclosing plant material. Sealed vessels 12 are translucent and permeable to gases and liquids for proper growth and development of the plant material contained therein. However, sealed vessels 12 are also impermeable to microorganisms for protecting the plant material against biological contamination.

Sealed vessels 12 are supported in a vessel support tray 14. Specifically, vessel support tray 14 includes a top plate 16 defining a plurality of holes 18 for receiving sealed vessels 12. A pair of vessel support trays are shown in series in FIG. 1 in order to demonstrate the capability of the present invention to mass produce small plants. For instance, many more support trays 14 can be added to plant propagation system 10 depending upon the number of small plants that need to be grown or transported. As further shown in FIG. 1, vessel support trays 14 are connected to a network of tubing or conduit for carrying fluids to and from the trays for absorption by the plant material through sealed vessels 12.

Generally, plants need oxygen, carbon dioxide, water, nutrients, and light for carrying out respiration and growth processes. Oxygen, carbon dioxide and light can be provided to the plant material from the atmosphere. For providing nutrients, plant propagation system 10 includes a pair of fluid nutrient tanks 20A and 20B for containing a liquid growth media. The liquid growth media preferably contains nutrients necessary for plant growth at optimal concentrations. Well known liquid growth medias which can be incorporated into the present invention include Hoagland's hydroponic solution and Murashige and Skoog tissue culture media formulation. Ideally, when placed in plant propagation system 10, the growth of the plant material is done predominantly through photosynthesis or, in other words, autotrophically. As such, the plant growth media preferably does not contain high concentrations of sugars or other organic carbons. However, organic carbon can be present in the liquid solution, especially if the plant material is still dependent upon heterotrophic growth.

As shown, fluid nutrient tanks 20A and 20B are in the form of large five gallon containers. However, any type or size of container or any other means of providing a liquid nutrient solution to plant propagation system 10 is within the scope of the present invention. This includes systems to mix and proportion nutrient solutions. As illustrated in FIG. 1, fluid nutrient tanks 20A and 20B are respectively connected to fluid intake lines 22A and 22B which, in turn, empty into vessel support trays 14. The flow of the liquid nutrient solution into plant propagation system 10 is controlled by a pair of valves 24A and 24B.

The liquid growth media contained within nutrient tanks 20A and 20B flows by gravity or is pumped into vessel support trays 14 where the liquid nutrient solution is maintained at a level for continuous contact with sealed vessels 12, as will be described hereinafter. Preferably, the liquid growth media is provided to vessel support trays 14 in a batch-type manner instead of continuously flowing through the system. The plant material will more readily absorb the nutrient solution if the solution is kept in static contact with sealed vessels 12.

From vessel support trays 14, the liquid growth media is preferably discharged out recirculation lines 26A and 26B which are controlled by valves 28A and 28B, respectively. From recirculation lines 26A and 26B, the growth media is captured in corresponding recirculation tanks 30A and 30B. Once recaptured, the spent liquid growth media can be processed in order to ensure proper concentrations of ingredients and then reintroduced into plant propagation system 10.

Alternatively, the spent liquid growth media can be discharged from vessel support trays 14 out through discharge lines 32A and 32B which are controlled by corresponding valves 34A and 34B. Discharge lines 32A and 32B can be connected to other containers, tanks, plant systems or to a waste system for disposing of the spent solution.

Plant propagation system 10 further includes a water line 36 for connection to a water source such as a tank, reservoir, hose or faucet. Water line 36 provides water to system 10 through fluid intake lines 22A and 22B. The flow of water into lines 22A and 22B is controlled by valves 38A and 38B, respectively. Water is provided to plant propagation system 10 for the purpose of absorption by the plant material or for rinsing the equipment. When being absorbed by the plant material, water is circulated into vessel support trays 14 where it is maintained at a level so as to remain in contact with sealed vessels 12.

Water can be provided to vessel support trays 14 in a batch system or can continuously flow through the trays. In a batch system, the water can be more easily absorbed by the plant material. However, a continuous flow system can be used to maintain a constant temperature within vessel support trays 14. For instance, cool water can be circulated in trays 14 for preventing exposure of the plant tissue to high temperatures. In a similar manner, warm water can be circulated through trays 14 for raising the temperature within plant propagation system 10. Once circulated through vessel support trays 14, the water can be discharged or recycled through discharge lines 32A and 32B.

Of course, if a batch system is desired, other means can be used to maintain constant and optimal temperatures within sealed vessels 12. For instance, vessel support trays 14 can include heaters or coolers for heating or cooling the sealed vessels contained therein.

During photosynthesis, besides carbon dioxide and light energy, the plant material needs water, in order to synthesize carbohydrates. Consequently, in one preferred embodiment, water is circulated through vessel support trays 14 during daylight hours for absorption by the plant material. In turn, the liquid growth media or nutrient solution is provided to the plant material at night. This system also limits the growth of algae or other autotrophic plants from growing and multiplying in the liquid growth media when circulated in the vessel support trays during the day.

However, the liquid growth media can include water as an ingredient in concentrations sufficient to support photoautotrophic growth. As such, the liquid growth media alternatively can be circulated in trays 14 during the day without slowing or decreasing the growth rate of the plant material.

As an optional feature, plant propagation system 10 can further include a disinfectant tank 40 for containing a disinfectant solution. Disinfectant tank 40 is connected to a disinfectant line 42 which flows into fluid intake lines 22A and 22B. The flow of disinfectant into system 10 is controlled by valves 44A and 44B.

A disinfectant solution can be circulated through plant propagation system 10 for destroying and inhibiting the growth of any microorganisms including bacteria, fungus, molds, yeasts, and especially algae. Because plant propagation system 10 is designed for plant growth, algae and other small plants can thrive within the system. Once present, the algae can cause a number of problems. For instance, algae can block needed light from the plant material, can absorb and deplete the liquid growth media or water, and can attach themselves to the outside of sealed vessels 12 inhibiting the flow of fluids into the vessels. Fortunately, as described above, algae, insects and all other microorganisms are not able to cross into the sealed vessels.

In order to maintain an aseptic environment and in order to remove all biological contaminants, the disinfectant solution can be circulated through the network of tubing and through vessel support trays 14. Further, the disinfectant solution can harmlessly wash over sealed vessels 12 without injuring the plant material contained therein. As such, the disinfectant should remain within system 10 for a period of time sufficient to destroy microorganisms but for a period of time insufficient to permit the disinfectant to diffuse into sealed vessels 12. Further, after circulating the disinfectant solution, system 10 should be rinsed with water flowing in from water line 36. In a preferred embodiment, the disinfectant solution is circulated through system 10 approximately every three days and is immediately followed by three different water rinse cycles.

There are many different types of disinfectant solutions that can be used in plant propagation system 10. As one example, the disinfectant can include a solution of sodium hypochlorite or bleach. Preferably, the bleach is in a concentration of from about 0.1% to about 10% by volume. Of course, many other disinfectants can be used and selected. Preferably, a disinfectant will be chosen that works particularly well against the microorganisms to be controlled.

Another feature which can optionally be added to plant propagation system 10 is a central control device generally 46. In the embodiment illustrated, central control device 46 includes a control box 48 and a computer or microprocessor 50. As shown in FIG. 1, an electrical connecting means 52 connects control box 48 to each and every valve within plant propagation system 10. As such, central control device 46 can be programmed to control the flow of fluids into and out of plant propagation system 10. Specifically, computer 50 can be programmed to open and close the fluid valves in a preselected pattern at predetermined times for maintaining optimal growth conditions and for disinfecting the system. Preferably, the valves installed within the system are solenoid valves capable of being controlled electronically. Central control device 46 can be used to totally automate the system for the mass production of plant material.

Figure 2:
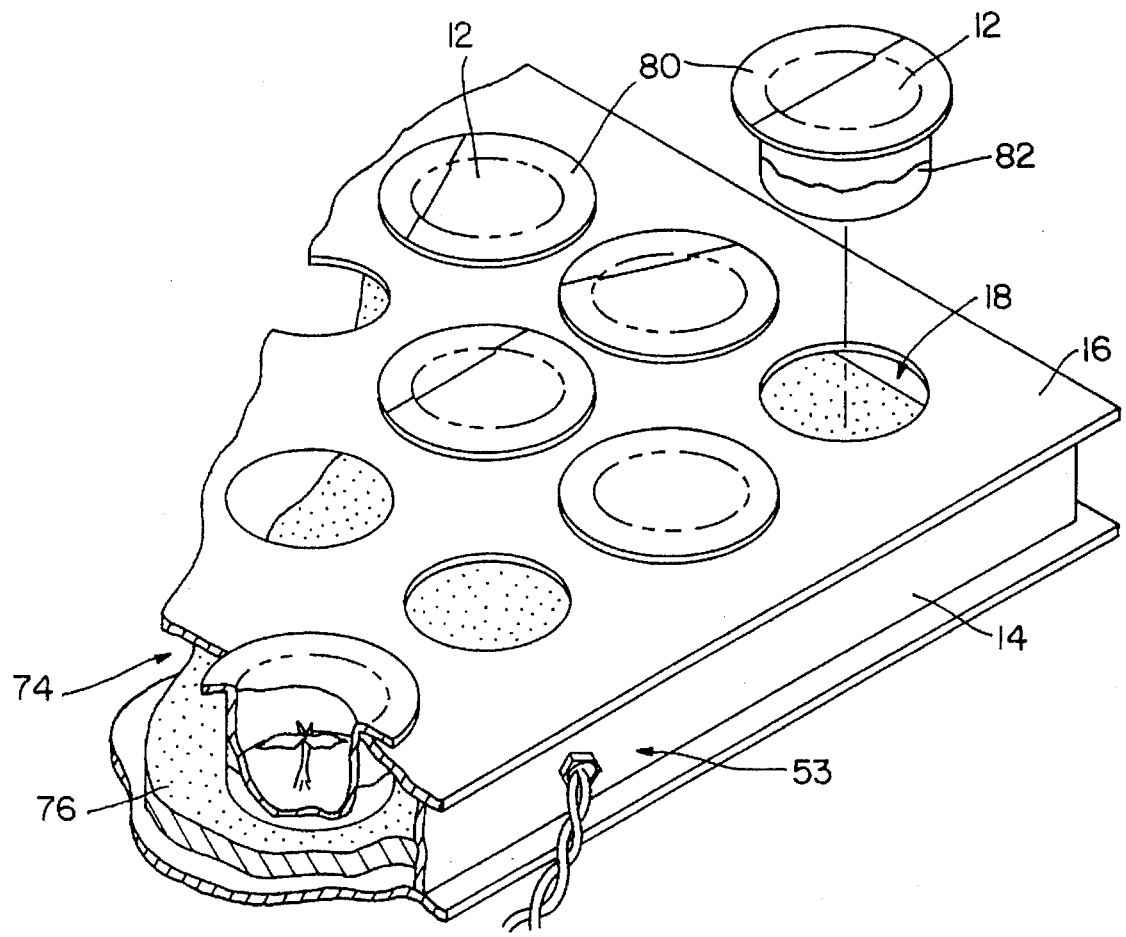
FIG. 2 is a partial perspective view with cutaway portions of an embodiment of a vessel support tray with accompanying sealed, semipermeable membrane vessels as in accordance with the present invention.

Besides regulating and controlling the flow of fluids, central control device 46 can be connected to a number of instruments or probes generally 53 as illustrated in FIG. 2 for monitoring conditions within plant propagation system 10. For instance, system 10 can further include a temperature sensing means for determining the temperature of fluids at different locations within the system. Such temperature measuring devices include, for example, thermocouples which are capable of transmitting information to computer or microprocessor 50. The temperature sensed by these devices can ultimately appear upon a screen or printed on a chart. Further, central control device 46 can be programmed with warning limits such that when certain temperatures are reached, a warning light or an audible alarm is activated.

In a further embodiment, central control device 46 can be used to not only monitor system conditions but to also automatically make changes and corrections within the system. For instance, if the temperature within vessel support trays 14 were to increase beyond a desired limit, central control device 46 can be programmed to automatically take action for reducing the temperature such as, for example, circulating cool water or activating a cooling device.

Other similar instruments that can be incorporated into the plant propagation system of the present invention include pH monitors for monitoring the pH of liquids, humidity devices, or even a conductivity meter for measuring the conductivity of the liquid growth media for ensuring that it contains proper concentrations of nutrients. As described above, central control device 46 can automatically receive information from these instruments for transmitting it to a user. Further, other similar warning devices or corrective means can be installed for preventing harm to the plant material while maintaining optimal growth conditions.

As described, plants require carbon dioxide in order to carry out photosynthesis for producing carbohydrates. In the past, when sealed in containers, plants have been reluctant to photosynthesize. A possible cause for this deficiency may result from the depletion of carbon dioxide within the container. In order to overcome this problem, plant propagation system 10 can optionally include a pure carbon dioxide source 54 as illustrated in FIG. 1. Carbon dioxide source 54 is connected to vessel support trays 14 via a carbon dioxide line 56. As such, carbon dioxide at any preferred concentration can be fed to vessel support trays 14 for absorption by the plant material in order to promote photosynthesis.

A further optional feature that can be added to plant propagation system 10 is a spectral or optical filter for filtering the light before it reaches the plant material. For instance, when plants first arrive from a laboratory, solar radiation may be too intense for chloroplasts developed under low light conditions. Also, some plants tend to grow better when only exposed to light in a particular range of wavelengths. Particularly, red light has been demonstrated to increase growth rates in some plant species.

Figure 5:
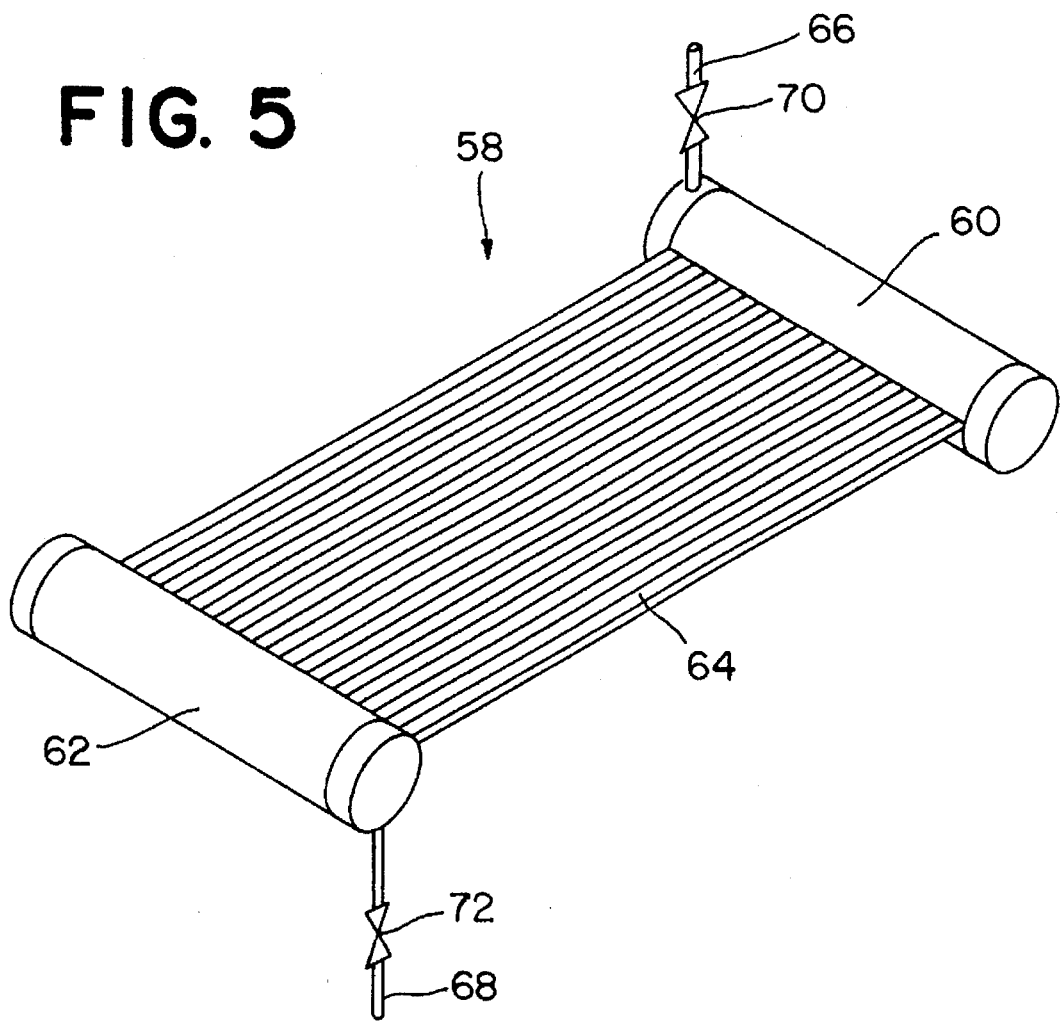
FIG. 5 is a perspective view of an embodiment of a spectral filter in accordance with the present invention.

In FIG. 1, one embodiment of a spectral filter 58 is shown in phantom and which is better illustrated in FIG. 5. As shown in the figures, spectral filter 58 is designed to contain a colorized liquid for filtering light. Referring to FIG. 5, spectral filter 58 includes channelized glazing 64 extending in between an intake chamber 60 and an exit chamber 62. The colorized liquid is added to spectral filter 58 through an intake line 66 and can be emptied through an exit line 68. The flow of the colorized liquid in and out of spectral filter 58 is controlled by an intake valve 70 and an exit valve 72. Channelized glazing 64 is preferably made of a translucent polycarbonate material. Such material is sold under the trade name POLY-GAL by the Exolite Company from Cedar Knolls, N.J.

When filled with the colorized liquid, spectral filter 58 can be placed over vessel support tray 14 as shown in FIG. 1. Any colorized liquid can be used within spectral filter 58 depending upon the desired wavelengths of light that are to reach the plant material. One particular liquid that will permit transmission of red light is a copper sulfate solution. Preferably, the copper sulfate is in solution at a concentration of about 3% to about 10%.

Additionally, spectral filter 58 can be used for controlling temperatures within vessel support tray 14. For instance, the light filtering liquid or even water can be circulated at particular temperatures above the growing plant material in order to maintain particular temperatures within the system.

For example, a cool liquid can be circulated through spectral filter 58 in close proximity to vessel support tray 14 for preventing the plant material from being overheated. Further, a pair of spectral filters 58 can be stacked in order to simultaneously filter light and circulate water at a particular temperature.

Of course, any other means of filtering light can be used in the system and process of the present invention. Other ways to isolate particular wavelengths of light include using colorized panels or even using particular light bulbs or light sources.

Referring now to FIGS. 2, 3, 4 and 4A, the vessel support tray and the sealed, semipermeable membrane vessels will be described in more detail. In FIG. 2, a portion of vessel support tray 14 as shown in FIG. 1 is illustrated. As described above, vessel support tray 14 includes top plate 16 defining a plurality of holes 18 for receiving sealed, semipermeable membrane vessels 12. As shown, sealed vessels 12 include a top flanged end defining a rim 80 and a bottom end 82. Bottom end 82 is inserted into corresponding hole 18 such that rim 80 remains supported upon top plate 16. As such, bottom end 82 remains suspended from top plate 16 for contact with fluids circulated within vessel support tray 14. Of course, any other means for providing contact between sealed vessel 12 and the circulating fluids is within the scope of the present invention.

Below top plate 16 of vessel support tray 14 there is a fluid retaining chamber generally 74 for circulating liquids and gases within the tray. A liquid 76 is shown in FIG. 2 within fluid retaining chamber 74 for contact with sealed vessels 12. Preferably, liquid 76 is maintained at a level for continuous and uninterrupted contact with sealed vessels 12 without overflowing from vessel support tray 14. In order to control the level of liquid 76 within vessel support tray 14, many different methods can be employed. For instance, a flow meter or a load cell can be installed within plant propagation system 10 for measuring the volume or weight of the liquid as it flows into vessel support tray 14. Other alternative means can include installing level indicators or overflow lines within vessel support tray 14. Further, any of these methods can be controlled by central control device 46 as illustrated in FIG. 1.

Besides liquids, gases can also be circulated within fluid retaining chamber 74 of vessel support tray 14. The gases such as oxygen or carbon dioxide can be circulated alone or in conjunction with liquids. If added simultaneously with the liquids, the gases can occupy the space in between the liquid level and top plate 16. Further, sealed vessels 12 can be constructed in order to absorb simultaneously the liquids and gases circulated within vessel support tray 14 as will be described hereinafter.

Figure 3:
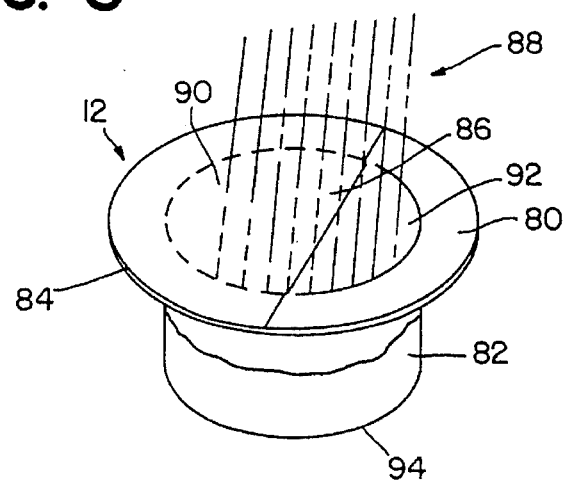
FIG. 3 is a perspective view of an embodiment of a sealed, semipermeable membrane vessel in accordance with the present invention.

Referring to FIG. 3, one embodiment of sealed, semipermeable membrane vessel 12 for completely enclosing plant material therein is illustrated. As described above, sealed vessel 12 is permeable to gases and liquids while remaining impermeable to microorganisms and other biological contaminants. Specifically, sealed vessel 12 includes a top end 84 and bottom end 82. Top end 84 includes a top membrane portion 86. In the embodiment shown in FIG. 3, top membrane portion 86 is divided into a first section 90 and a second optional section 92. Preferably, first section 90 is made from a translucent film for allowing light rays 88 to enter sealed vessel 12 for absorption by the plant material. First section 90 is also preferably permeable to gas but impermeable to microorganisms. An example of a membrane with the desired characteristics is an unstretched polypropylene film marketed by Hoechst celanese, Inc. in Charlotte, N.C. The film has a pore size of approximately 0.01 microns for permitting the passage of gases. However, a membrane can be used which is also permeable to liquids as long as the membrane permits light transmission and prevents the influx of microorganisms.

Second section 92 of top membrane portion 86, on the other hand, is preferably gas permeable and liquid permeable while still remaining impermeable to biological contaminants. Second section 92 can be included with sealed vessel 12 when first section 10 is only permeable to gases. Specifically, second section 92, although optional, has been added so that water vapor can more easily diffuse in and out of sealed vessel 12. As such, the humidity in the ambient environment is maintained in equilibrium with the humidity levels inside of sealed vessel 12. To achieve this result, second section 92 is preferably made from a film that is not hydrophobic with a pore size no larger than about 0.2 microns. An example of such a film is marketed under the trade name CELGARD which is a treated polypropylene film having a pore size of approximately 0.075 microns. Specifically, the CELGARD film is made by stretching and treating the clear polypropylene film described above. CELGARD film is also sold by Hoechst Celanese, Inc. in Charlotte, N.C. For purposes of comparison, the smallest microorganisms such as bacteria and viruses have a size of approximately 0.2 to 0.5 microns. As such, these organisms are not capable of passing through the above-described membranes.

In order to attach first section 90 to second section 92, the films are preferably heat-sealed together at adjoining ends. However, the films may be joined together or fixed to sealed vessel 12 in a variety of other ways and methods. Also, in another embodiment of sealed vessel 12, top membrane portion 86 is made from only one single type of membrane. For instance, top membrane portion 86 can be made entirely from the unstretched polypropylene film. Generally, top membrane portion 86 should be translucent.

Further, top membrane portion 86 is also preferably heat sealed to top end 84. As such, sealed vessel 12 is preferably made from a structural plastic material or a similar material that is capable of being heat sealed to thermoplastic film. Of course, sealed vessel 12 can be made from many other different structural materials including metals by employing a different means of attaching top membrane portion 86.

Sealed vessel 12 also includes a bottom end 82 having a bottom membrane portion 94. Bottom membrane portion 94 is preferably gas and liquid permeable and is also preferably located on the very bottom of sealed vessel 12 for allowing the plant material contained therein to absorb liquid 76 as shown in FIG. 2. In a preferred embodiment, bottom membrane portion 94 is made from the CELGARD polypropylene film marketed by Hoechst Celanese. The film can be heat sealed to bottom end 82 as shown in FIG. 3.

Sealed vessels 12 can also optionally include a means for supporting the root structure of growing plant tissue if needed. For instance, the plant material can be placed on a piece of porous material inside of the sealed vessels. Preferably, the material is porous for allowing roots to extend therein and for allowing absorbed liquids to reach the plant tissue. One particular material well suited for supporting root systems without interfering with the growth of the plants is cellulose. Further, cellulose is biodegradable and need not be separated from the plant when transplanted to soil.

As constructed, sealed, semipermeable membrane vessel 12 is generally translucent and gas permeable on the top and liquid permeable on the bottom while remaining impermeable to biological contaminants. As such, plant material, enclosed within the sealed vessels, can receive light, oxygen, carbon dioxide, water, nutrients and other growth and respiratory needs while remaining shielded against pathogenic microorganisms. The plant material such as vegetative buds, bulbets, PLB, microtubers, or somatic embryos can be placed within the sealed vessels when capable of forming shoots, but ill-suited for autotrophic growth. At this stage, the sealed vessel can be exposed to a liquid solution containing organic carbon for the heterotrophic growth and development of the plant. Once the plant material becomes capable of photosynthesizing, the sealed vessel can be placed within the plant propagation system as illustrated in FIG. 1 for promoting photoautotrophic growth. Once developed into a small plant capable of surviving in soil, the plant material can be transplanted as desired. Consequently, the plant material can be developed into a photosynthetic plantlet without ever being removed from the sealed vessels. Further, the sealed vessels can be used to facilitate transportation of the plant material to any desired location. For instance, vegetative material is prohibited from international commerce due to possible accidental inclusions of biological contaminants on plant tissue or media. As plants in this invention are produced free from biotic contaminants, and on sterile substrata, quarrantine regulations would be satisfied.

Figure 4:
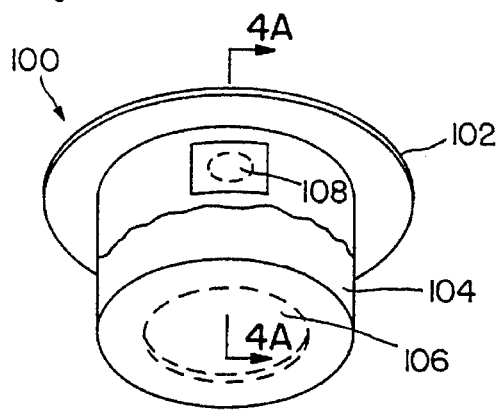
FIG. 4 is a perspective view of another embodiment of a sealed, semipermeable membrane vessel in accordance with the present invention.
Figure 4A:
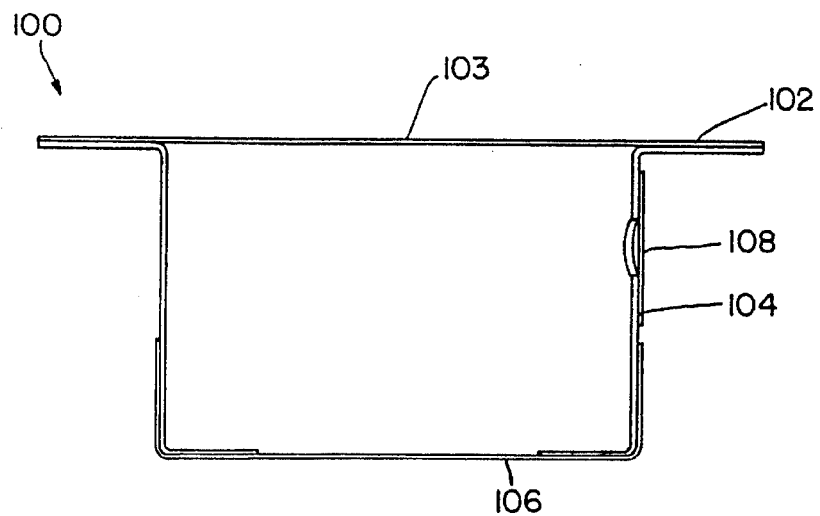
FIG. 4A is a side view taken along lines 4A—4A of FIG. 4.

Referring to FIGS. 4 and 4A, another embodiment of a sealed, semipermeable membrane vessel generally 100 is shown. Referring to FIG. 4, sealed vessel 100 includes a top and 102 and a bottom end 104. As illustrated in FIG. 4A, top end 102 includes a translucent top membrane portion 103 which is translucent, permeable to gases but impermeable to microorganisms.

Bottom end 104 includes a bottom membrane portion 106 and a side membrane portion 108. As before, bottom membrane portion 106 is permeable to liquids and gases while remaining impermeable to microorganisms. When included, side membrane portion 108, is also preferably permeable to gases and liquids while preventing the passage of biological contaminants. Side membrane portion 108 is primarily designed to allow the plant material to absorb carbon dioxide when it is fed to the plant propagation system. When sealed vessel 100 is placed in vessel support tray 14, side membrane portion is designed to be located between top plate 16 and a level of liquid 76 as shown in FIG. 2. As described above, carbon dioxide is needed for photosynthesis and can be the rate determining constituent of the process. Consequently, depending upon the amount of carbon dioxide needed by the plant material, side membrane portion 108 can be increased or decreased in surface area. Further, a plurality of side membrane portions can be added to sealed vessel 100.

In FIG. 4A, a cross-section of sealed vessel 100 is illustrated showing top membrane portion 103, side membrane portion 108 and bottom membrane portion 106. Specifically, the liquid permeability of bottom membrane portion 106 is demonstrated.

The plant propagation system and method of the present invention may be better understood by reference to the following examples.

EXAMPLE I

Tissue samples of "Brassolaeliocattleya" (Mount Hood Mary) orchid plants were placed in three different embodiments of the sealed, semipermeable membrane vessels of the present invention. Specifically, each embodiment comprised a set of 16 sealed vessels so that there were 48 vessels total used in the experiment.

In one set, the sealed vessels included a top membrane portion made from a CELGARD film that is permeable to liquids and gases and impermeable to microorganisms. The film is not translucent and has a pore size of approximately 0.075 microns. In a second set of sealed vessels, the top membrane portion was made from a translucent polypropylene film that is only permeable to gases. The polypropylene film, having a pore size of approximately 0.01 microns, is an unstretched precursor film to the CELGARD film. A third set of sealed vessels included a top membrane portion having a section made from the CELGARD film heat sealed along adjoining edges to another section made of the translucent polypropylene film. All of the sealed vessels used in the experiment also included a bottom membrane portion made from CELGARD film which, as described above, is gas and liquid permeable.

The plant tissue contained within the sealed vessels were first grown heterotrophically in a laboratory. Specifically, the sealed vessels were enclosed in polycarbonate boxes containing a liquid growth medium for contact with the bottom of the sealed vessels for absorption by the plant tissue. Each polycarbonate box held about 10 sealed vessels. The growth medium was a Murashige and Skoog tissue culture media formulation including 3% sucrose. The Murashige and Skoog formulation is as follows:

| Component | Amount (mg/L) |
| --- | --- |
| Ammonium Nitrate | 1650.0 |
| Boric Acid | 6.2 |
| Calcium Chloride Anhydrous | 332.2 |
| Cobalt Chloride $6H_2O$ | 0.025 |
| Cupric Sulfate $5H_2O$ | 0.025 |
| $Na_2$-EDTA | 37.25 |
| Ferrous Sulfate $7H_2O$ | 27.8 |
| Magnesium Sulfate | 180.7 |
| Manganese Sulfate $H_2O$ | 16.9 |
| Molybdic Acid (Sodium Salt) $2H_2O$ | 0.25 |
| Potassium Iodide | 0.83 |
| Potassium Nitrate | 1900.0 |
| Potassium Phosphate Monobasic | 170.0 |
| Zinc Sulfate $7H_2O$ | 8.6 |
| Grams of Powder to prepare 1 liter = | 4.3 |
| pH at room temperature = | 3.8 |

After 104 days in the laboratory, the sealed, semipermeable membrane vessels were transported to a greenhouse and placed in the plant propagation system of the present invention. The plant tissue was grown in the greenhouse in the vessel support trays for 52 days. During daylight hours, distilled water was circulated through the vessel support trays while at night, a nutrient solution was circulated. Specifically, the nutrient solution was Hoagland's hydroponic solution having the following formulation:

| Component | Amount |
| --- | --- |
| Ammonium Phosphate Monobasic | 115.03 |
| Boric Acid | 2.80 |
| Calcium Nitrate | 646.4 |
| Cupric Sulfate $5H_2O$ | 0.08 |
| Ferric Tartrate $2H_2O$ | 5.32 |
| Magnesium Sulfate | 240.76 |
| Manganese Chloride $4H_2O$ | 1.81 |
| Molybdenum Trioxide | 0.016 |
| Potassium Nitrate | 606.6 |
| Zinc Sulfate $7H_2O$ | 0.22 |

-continued

| Component | Amount |
| --- | --- |
| Grams of Powder to prepare 1 liter = | 1.6 |
| pH at room temperature = | 4.7 |

Once a day a disinfectant was circulated through the system followed by three rinse cycles of distilled water. The disinfectant was a 5.0% sodium hypochlorite solution. The following growth occurred during the course of the experiment:

| Top Membrane Portion | Avg. Initial Weight (g) | Avg. Weight After 104 days in Laboratory (g) | Avg. Wgt. After 62 days in Plant Propagation System in Greenhouse (g) |
| --- | --- | --- | --- |
| Translucent Polypropylene, | 0.18 | 1.73 | 2.44 |
| CELGARD, | 0.17 | 1.27 | 1.10 |
| Polypropylene/ CELGARD, | 0.26 | 1.01 | 1.44 |

As shown, the plant propagation system of the present invention is capable of promoting the photoautotrophic growth of plant tissue samples. Further, the sealed, semipermeable membrane vessels are useful in both initial heterotrophic growth and photoautotrophic growth. From the above, it appears that it is best to use the translucent polypropylene film for the top membrane portion of the sealed vessels. Although unknown, this result is most likely due to the fact that more light enters the sealed vessels when using the polypropylene film.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. It will also be understood that although the forms of the invention shown and described herein constitute a preferred embodiment of the invention, it is not intended to illustrate all possible forms of the invention. The words used are words of description rather than of limitation. Various changes and variations may be made to the present invention without departing from the spirit and scope of the following claims.

What is claimed is:

1. A plant propagation system comprising:

at least one sealed, semipermeable membrane vessel for containing growing plant material therein, said at least one vessel including a first membrane portion and a second membrane portion, said first membrane portion being at least permeable to gases while remaining impermeable to microorganisms, said second membrane portion being at least permeable to liquid while remaining impermeable to microorganisms;

a vessel support tray for receiving said at least one sealed, semipermeable membrane vessel, said vessel support tray including a fluid retaining chamber adapted to contain and circulate various fluids for contact with said at least one vessel;

a growth media reservoir means for supplying a growth media to said fluid retaining chamber of said vessel support tray for diffusion into said at least one sealed vessel;

valved conduit means for connection between said vessel support tray and said growth media reservoir means and for regulating the flow of said growth media therebetween; and central control means in communication with at least one element of said system for automatically controlling thereof.

2. The plant propagation system as defined in claim 1, wherein said central control means comprises a programmable electronic device including a microprocessor.

3. The plant propagation system as defined in claim 1, further including a disinfectant reservoir in fluid connection with said support tray for periodically supplying a disinfectant to said vessel support tray for destroying microorganisms and algae within said tray and on the outside of said sealed vessels.

4. The plant propagation system as defined in claim 3, wherein said central control means is electrically connected with said disinfectant reservoir whereby the flow of said disinfectant is controlled and regulated by said central control means.

5. The plant propagation system as defined in claim 3, further including a water source in fluid connection with said support tray for supplying water to said system.

6. The plant propagation system as defined in claim 1, further including monitoring means for monitoring at least one system condition.

7. The plant propagation system as defined in claim 6, wherein said monitoring means includes a pH meter, a conductivity meter, and a temperature probe for respectively monitoring the pH, the conductivity and the temperature of fluids circulating in said vessel support tray.

8. The plant propagation system as defined in claim 1, further including a carbon dioxide source in fluid connection with said support tray for supplying carbon dioxide to said vessel support tray for diffusion into said sealed vessels.

9. The plant propagation system as defined in claim 1, further comprising a spectral filter located above said vessel support tray for filtering light such that light rays at a certain wavelength reach said plant tissue for promoting and increasing plant growth.

10. A plant propagation system for aseptically growing plant tissue and producing small plants capable of being transplanted into soil, said system comprising:

a plurality of sealed, semipermeable membrane vessels for containing growing plant material therein, each of said vessels having a first portion that is at least permeable to gases and a second portion that is at least permeable to liquids, said first and second portions being impermeable to microorganisms, wherein said vessels allow necessary nutrients and gases to diffuse therein for promoting the development of said plant material while preventing the influx of biological contaminants;

a vessel support tray having a top plate, said top plate defining a plurality of openings for receiving said semipermeable vessels, said tray including a fluid retaining chamber adapted to contain and circulate various fluids for contact with said vessels;

a growth media reservoir in communication with said tray for supplying a growth media thereto for absorption by said plant material;

a disinfectant reservoir in communication with said tray for supplying a disinfectant thereto for destroying biological contaminants;

a water source in communication with said tray for supplying water thereto; and means for controlling fluid flow to said tray.

11. The plant propagation system as defined in claim 10, further comprising a central control means for controlling the flow of fluids within said system.

12. The plant propagation system as defined in claim 11, wherein said central control means comprises a programmable electronic device including a microprocessor.

13. The plant propagation system as defined in claim 10, further including monitoring means for monitoring at least one system condition.

14. The plant propagation system as defined in claim 10, further comprising a cooling and heating means for maintaining an optimal temperature within said sealed vessels.

15. The plant propagation system as defined in claim 10, wherein said top plate of said vessel support tray is translucent.

16. The plant propagation system as defined in claim 10, wherein each of said sealed vessels includes a porous root structure means for supporting any root structure growing from said plant material.

17. The plant propagation system as defined in claim 16, wherein said root structure means includes a cellulose plug.

18. The plant propagation system as defined in claim 10, wherein said first portion of said sealed vessels comprises translucent polypropylene film while said second portion is a stretched microporous polypropylene film.

19. The plant propagation system as defined claim 18, wherein a section of said first portion is a stretched microporous polypropylene film.

20. The plant propagation system as defined in claim 10, further comprising a carbon dioxide source in communication with said tray for supplying carbon dioxide thereto for diffusion into said sealed vessels for use by said plant material.

21. The plant propagation system as defined in claim 10, further comprising a spectral filter located above said vessel support tray.

22. The plant propagation system as defined in claim 21, wherein said spectral filter includes translucent channelized glazing filled with a light filtering liquid.

23. The plant propagation system as defined in claim 22, wherein said light filtering liquid is a solution of copper sulfate for transmitting red light to said plant material.

24. An automated plant propagation system, said system comprises:

a plurality of sealed, semipermeable membrane vessels for completely enclosing and sustaining the growth of plant tissue therein, said vessels having a top flanged end and a bottom end, said top flanged end defining a rim and including a top membrane portion sealed to said top flanged end which is translucent and gas permeable but which is impermeable to microorganisms, said bottom end having a bottom membrane portion which is liquid permeable and impermeable to microorganisms, wherein said vessels allow necessary nutrients, liquids, gases and light to diffuse therein for the growth and development of said plant tissue while preventing influx of biological contaminations;

a vessel support tray having a top plate, said top plate defining a plurality of openings for receiving said bottom end of said semipermeable vessels therein such that said rim of said vessels remains supported upon said top plate, said vessel support tray including a fluid retaining chamber beneath said top plate adapted to contain and circulate various fluids for contact with said vessels;

a growth media reservoir means connected to said vessels support tray for supplying a growth media to said fluid retaining chamber for absorption by said plant tissue through said bottom membrane portion;

valve means for regulating the flow of said growth media to said fluid retaining chamber; and central control means for automatically controlling said valve means and for maintaining levels of said growth media within said vessel support tray, wherein said plant tissue is developed into small plants by absorbing said growth media, gases and light while remaining enclosed within said sealed vessels.

25. The plant propagation system as defined in claim 24, further including a disinfectant reservoir means connected to said vessel support tray and said control means for periodically supplying a disinfectant to said tray for destroying microorganisms and algae within said tray and on the outside of said sealed vessels, wherein the flow of said disinfectant is controlled by said central control means.

26. The plant propagation system as defined in claim 25, further including a water source connected to said tray and said control means for supplying water to said system, the flow of water from said source being controlled by said central control means.

27. The plant propagation system as defined in claim 24, wherein said central control means comprises a programmable electronic device including a microprocessor.

28. The plant propagation system as defined in claim 24, further including monitoring means connected to said central control means and said tray for monitoring at least one system condition.

29. The plant propagation system as defined in claim 24, wherein said sealed vessels include side membrane portions that are gas permeable and wherein said system further comprises a carbon dioxide source connected to said tray for supplying carbon dioxide thereto for diffusion into said vessels for use by said plant material.

30. The plant propagation system as defined in claim 24, further Comprising a spectral filter means located above said vessel support tray for filtering light such that only light rays at a certain wavelength reach said plant tissue for promoting and increasing growth.

* * * * *

UNITED STATES PATENT AND TRADEMARK OFFICE
CERTIFICATE OF CORRECTION

PATENT NO. : 5,597,731
DATED : January 28, 1997
INVENTOR(S) : Roy E. Young and Jeffrey W. Adelberg It is certified that error appears in the above-identified patent and that said Letters Patent is hereby corrected as shown below:

Column 14,
Line 44, please delete "3.8" and insert therefor -- 3.9 --.

Signed and Sealed this

Twenty-ninth Day of January, 2002

Attest:

JAMES E. ROGAN
*Attesting Officer*     *Director of the United States Patent and Trademark Office*